United States Patent
Hickmann et al.

(10) Patent No.: US 12,187,978 B2
(45) Date of Patent: Jan. 7, 2025

(54) USE OF (3-ACETOXY-2,2-DIMETHYL-PROPYL) ACETATE IN COMBINATION WITH (3-HYDROXY-2,2-DIMETHYL-PROPYL) ACETATE AS AN AROMA CHEMICAL

(71) Applicant: BASF SE, Ludwigshafen am Rhein (DE)

(72) Inventors: Volker Hickmann, Ludwigshafen am Rhein (DE); Manuel Danz, Ludwigshafen am Rhein (DE); Florian Garlichs, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 710 days.

(21) Appl. No.: 17/433,741

(22) PCT Filed: Feb. 14, 2020

(86) PCT No.: PCT/EP2020/053955
§ 371 (c)(1),
(2) Date: Aug. 25, 2021

(87) PCT Pub. No.: WO2020/173726
PCT Pub. Date: Sep. 3, 2020

(65) Prior Publication Data
US 2022/0135901 A1    May 5, 2022

(30) Foreign Application Priority Data
Feb. 25, 2019 (EP) .................... 19159189

(51) Int. Cl.
*C11B 9/00* (2006.01)
*A61K 8/34* (2006.01)
*C11D 3/20* (2006.01)

(52) U.S. Cl.
CPC ................. *C11B 9/0019* (2013.01)

(58) Field of Classification Search
CPC ........ A61K 8/34; A61K 8/37; A61K 2800/59; C11B 9/0019; C11D 3/50; C11D 3/2093; A61Q 13/00

USPC ...................................... 512/25, 1
See application file for complete search history.

(56) References Cited

U.S. PATENT DOCUMENTS

2018/0037844 A1    2/2018 Foley et al.

FOREIGN PATENT DOCUMENTS

WO         98/32728 A1      7/1998
WO    WO-2016118882 A1 *    7/2016 ............. A23L 27/33

OTHER PUBLICATIONS

Szymanska et al, MsAcT in siliceous monolithic microreactors enables quantitative ester synthesis in water, 2016, Catal. Sci. Technol., 4882-4888 (Year: 2016).*
International Search Report and Written Opinion received for PCT Patent Application No. PCT/EP2020/053955, mailed on Apr. 24, 2020, 11 pages.
Katarzyna et al., MsAcT in siliceous monolithic microreactors enables quantitative ester synthesis in water, Catalysis Science & Technology, vol. 6, No. 13, 2016, pp. 4882-4888.
Lotte et al., "Transesterifications and Peracid-Assisted Oxidations in Aqueous Media Catalyzed by *Mycobacterium smegmatis* Acyl Transferase", CHEMCATCHEM, vol. 5, 2013, pp. 3719-3724.

* cited by examiner

*Primary Examiner* — Jessica Whiteley
(74) *Attorney, Agent, or Firm* — Faegre Drinker Biddle & Reath LLP

(57) ABSTRACT

The present invention relates to the use of (3-hydroxy-2,2-dimethyl-propyl) acetate for enhancing and/or modifying the aroma of (3-acetoxy-2,2-dimethyl-propyl) acetate. The invention further relates to the use of (3-acetoxy-2,2-dimethyl-propyl) acetate in combination with (3-hydroxy-2,2-dimethyl-propyl) acetate as an aroma chemical and for enhancing and/or modifying the aroma of a composition. The present invention further relates to compositions comprising (3-acetoxy-2,2-dimethyl-propyl) acetate combined with (3-hydroxy-2,2-dimethyl-propyl) acetate and at least one aroma chemical and/or at least one non-aroma chemical carrier.

15 Claims, No Drawings

USE OF (3-ACETOXY-2,2-DIMETHYL-PROPYL) ACETATE IN COMBINATION WITH (3-HYDROXY-2,2-DIMETHYL-PROPYL) ACETATE AS AN AROMA CHEMICAL

CROSS-REFERENCE TO RELATED APPLICATIONS

This application is a national stage application (under 35 U.S.C. § 371) of PCT/EP2020/053955, filed Feb. 14, 2020, which claims benefit of European Application No. 19159189.0, filed Feb. 25, 2019, both of which are incorporated herein by reference in their entirety.

The present invention relates to the use of (3-hydroxy-2,2-dimethyl-propyl) acetate for enhancing and/or modifying the aroma of (3-acetoxy-2,2-dimethyl-propyl) acetate. The invention further relates to the use of (3-acetoxy-2,2-dimethyl-propyl) acetate in combination with (3-hydroxy-2,2-dimethyl-propyl) acetate as an aroma chemical and for enhancing and/or modifying the aroma of a composition. The present invention further relates to compositions comprising (3-acetoxy-2,2-dimethyl-propyl) acetate combined with (3-hydroxy-2,2-dimethyl-propyl) acetate and at least one aroma chemical and/or at least one non-aroma chemical carrier.

BACKGROUND OF THE INVENTION

Aroma chemicals, especially fragrances, are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest to create synthetic substances which have organoleptic properties that resembles more expensive natural fragrances or which have novel and interesting organoleptic profiles.

Despite a large number of already existing aroma chemicals, there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other aroma chemicals, a higher stability under certain application conditions, a higher extendibility, a better staying power, etc.

Esters of 2,2-dimethyl-1,3 propanediol and aliphatic carboxylic acids, including neopentyl glycol diacetate (IUPAC name: (3-acetoxy-2,2-dimethyl-propyl) acetate) and neopentyl glycol monoacetate (IUPAC name: (3-hydroxy-2,2-dimethyl-propyl) acetate) as well as methods for their preparation are known for more than 20 years and have previously been described as components of film-forming agents of water-soluble paints (WO 98/32728). More recently, (3-acetoxy-2,2-dimethyl-propyl) acetate was described as a sweet, fresh and pleasing aroma (WO 2016/118882).

SUMMARY OF THE INVENTION

It was an object of the present invention to improve the aroma properties of (3-acetoxy-2,2-dimethyl-propyl) acetate, especially with regard to niceness, conciseness as well as intensity.

It was surprisingly found that the aroma of (3-acetoxy-2,2-dimethyl-propyl) acetate can be enhanced and/or modified by (3-hydroxy-2,2-dimethyl-propyl) acetate. Specifically, the aroma of the resulting mixture was found to have improved niceness and conciseness. In addition, the aroma of the resulting mixture was found to have improved intensity compared to the aroma of (3-acetoxy-2,2-dimethyl-propyl) acetate.

It was a further object of the present invention to provide substances, which can be used as aroma chemical. In was a further object of the present invention to provide substances which can be used in compositions, which preferably are aroma compositions, such for example in perfume compositions, body care compositions, hygiene articles, household cleaning compositions, textile detergent compositions, foods, food supplements, pharmaceutical compositions or crop protection compositions. In particular, substances having a pleasant odor are sought.

It was surprisingly found that, (3-acetoxy-2,2-dimethyl-propyl) acetate in combination with (3-hydroxy-2,2-dimethyl-propyl) acetate exhibits pleasant organo-leptic properties and can advantageously be used as an aroma chemical.

Accordingly, one embodiment of the present invention relates to the use of (3-hydroxy-2,2-dimethyl-propyl) acetate for enhancing and/or modifying the aroma of (3-acetoxy-2,2-dimethyl-propyl) acetate.

A further embodiment of the present invention relates to the use of (3-acetoxy-2,2-dimethyl-propyl) acetate in combination with (3-hydroxy-2,2-dimethyl-propyl) acetate as an aroma chemical.

The combination of (3-hydroxy-2,2-dimethyl-propyl) acetate and (3-acetoxy-2,2-dimethyl-propyl) acetate can be used in compositions where it can be combined with aroma chemicals to create new aroma profiles. A further embodiment of the present invention thus relates to the use of (3-hydroxy-2,2-dimethyl-propyl) acetate in combination with (3-acetoxy-2,2-dimethyl-propyl) acetate for enhancing and/or modifying the aroma of a chemical composition, which further comprises at least one aroma chemical, which is different from (3-hydroxy-2,2-dimethyl-propyl) acetate and (3-acetoxy-2,2-dimethyl-propyl) acetate.

A further embodiment of the present invention relates to a composition comprising (3-acetoxy-2,2-dimethyl-propyl) acetate combined with (3-hydroxy-2,2-dimethyl-propyl) acetate and:
  (i) at least one aroma chemical, or
  (ii) at least one non-aroma chemical carrier, or
  (iii) both of (i) and (ii).

Said at least one aroma chemical of (i) is different from (3-acetoxy-2,2-dimethyl-propyl) acetate and (3-hydroxy-2,2-dimethyl-propyl) acetate.

In a preferred embodiment of the invention, the composition is an aroma composition, more preferably an odor composition, more preferably a fragrance composition.

The composition according to the invention can be selected from, but is not limited to, the group consisting of perfume compositions, body care compositions (including cosmetic compositions and products for oral and dental hygiene), hygiene articles, cleaning compositions (including dishwashing compositions), textile detergent compositions, compositions for scent dispensers, foods, food supplements, pharmaceutical compositions and crop protection compositions.

A further embodiment of the present invention relates to a method of preparing a composition, the method comprising mixing (3-acetoxy-2,2-dimethyl-propyl) acetate and (3-hydroxy-2,2-dimethyl-propyl) acetate with at least one aroma chemical (i) and/or at least one non-aroma chemical carrier (ii) so as to obtain the composition. In said method, (3-acetoxy-2,2-dimethyl-propyl) acetate and (3-hydroxy-2,2-dimethyl-propyl) acetate can be added in the form of a mixture or composition comprising these two compounds (and thus concurrently) or separately (sequentially or concurrently).

A further embodiment of the invention relates to a method of providing an aroma to a composition, the method comprising incorporating (3-acetoxy-2,2-dimethyl-propyl) acetate and (3-hydroxy-2,2-dimethyl-propyl) acetate into a composition.

A further embodiment of the present invention relates to a method of enhancing and/or modifying the aroma of (3-acetoxy-2,2-dimethyl-propyl) acetate, the method comprising incorporating (3-hydroxy-2,2-dimethyl-propyl) acetate into a composition, which comprises (3-acetoxy-2,2-dimethyl-propyl).

A further embodiment of the present invention relates to a method of enhancing and/or modifying the aroma of a composition, the method comprising incorporating (3-acetoxy-2,2-dimethyl-propyl) acetate and (3-hydroxy-2,2-dimethyl-propyl) acetate into a composition, which comprises at least one aroma chemical different from (3-acetoxy-2,2-dimethyl-propyl) acetate and (3-hydroxy-2,2-dimethyl-propyl) acetate. In said method, (3-acetoxy-2,2-dimethyl-propyl) acetate and (3-hydroxy-2,2-dimethyl-propyl) acetate can be incorporated into the composition in the form of a mixture or composition comprising these two compounds (and thus concurrently) or separately (sequentially or concurrently).

The pleasant aroma, low volatility and excellent solubility make the combination of (3-acetoxy-2,2-dimethyl-propyl) acetate and (3-hydroxy-2,2-dimethyl-propyl) acetate a suitable component in compositions where a pleasing aroma is desirable. By virtue of their physical properties, said combination has particularly good, virtually universal solvent properties for aroma chemicals and other customary ingredients in compositions such as, in particular, fragrance compositions. Therefore, combinations of (3-acetoxy-2,2-dimethyl-propyl) acetate and (3-hydroxy-2,2-dimethyl-propyl) acetate as described herein are favorably combinable with aroma chemicals, allowing, in particular, the creation of aroma compositions, in particular fragrance compositions, having novel advantageous sensory profiles.

DETAILED DESCRIPTION OF THE INVENTION

Definitions

In the context of the present invention, the term "aroma" refers to a sensory property and comprises an odor and/or a flavor.

The term "aroma chemical" denotes a substance which is used to obtain a sensory or organoleptic (used interchangeably herein) impression and comprises its use to obtain an olfactory and/or a flavor impression. The term "olfactory impression" denotes an odor impression without any positive or negative judgement, while the term "scent impression" or "fragrance impression" (used interchangeably herein) as used herein is connected to an odor impression which is generally felt as pleasant. Thus a "fragrance" or "scent" denotes an aroma chemical, which predominately induces a pleasant odor impression. A flavor denotes an aroma chemical which induces a taste impression.

The term "aroma composition", as used herein, refers to a composition which induces an aroma. The term aroma composition comprises "odor composition" and/or "flavor composition". An odor composition being a composition, which predominately induces an odor impression, a flavor composition being a composition, which predominantly induces a taste impression.

The term odor composition comprises "fragrance composition" or "scent composition" (used interchangeably herein), which predominately induce an odor impression which is generally felt as pleasant.

It is within the scope of the invention that the aroma of the composition can be imparted by (3-acetoxy-2,2-dimethyl-propyl) acetate and/or (3-hydroxy-2,2-dimethyl-propyl) acetate, and/or (if present) by the at least one aroma chemical (i) that is different from (3-acetoxy-2,2-dimethyl-propyl) acetate and (3-hydroxy-2,2-dimethyl-propyl) acetate, or by any combination thereof.

The general hedonistic expressions "advantageous sensory properties" or "advantageous organoleptic properties" describe the niceness and conciseness of an organoleptic impression conveyed by an aroma chemical. "Niceness" and "conciseness" are terms which are familiar to the person skilled in the art, such as a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

The expressions "combination of", "in combination with" or "combined with" when used herein referring to the compositions, methods or the use of two compounds, e.g. the use of (3-acetoxy-2,2-dimethyl-propyl) acetate in combination with (3-hydroxy-2,2-dimethyl-propyl) acetate, take account of the fact that the two compounds do not need to be used in the form of a physical mixture of said compounds but can be used (e.g., added) separately. Thus, the use of (3-acetoxy-2,2-dimethyl-propyl) acetate in combination with (3-hydroxy-2,2-dimethyl-propyl) acetate as described herein means that both of these compounds are used either separately or in the form of a physical mixture or composition comprising both compounds. Where the compounds are used separately, they can be used (e.g. added) sequentially (i.e. one after the other) in any order, or concurrently (i.e. basically at the same time). In preferred embodiments of the present invention, (3-acetoxy-2,2-dimethyl-propyl) acetate and (3-hydroxy-2,2-dimethyl-propyl) acetate are used in the form of a physical mixture or composition comprising both of said compounds.

The term "boosting" or "boost" is used herein to describe the effect of enhancing and/or modifying the aroma of an aroma chemical or of a composition. The term "enhancing" comprises an improvement of the niceness and/or conciseness of an aroma and/or an improvement of the intensity. The term "modifying" comprises the change of an aroma profile.

The intensity can be determined via a threshold value determination. A threshold value of an odor is the concentration of a substance in the relevant gas space at which an odor impression can just still be perceived by a representative test panel, although it no longer has to be defined.

Booster effects are particularly desired in fragrance composition when top-note-characterized applications are required, in which the odor is to be conveyed particularly quickly and intensively, for example in deodorants, air fresheners or in the taste sector in chewing gums.

The terms "the invention relates to" and "the invention is directed to" are used synonymously throughout the invention. The terms "compound" and "substance" are used synonymously throughout the invention.

EMBODIMENTS OF THE INVENTION

It has surprisingly been found that (3-hydroxy-2,2-dimethyl-propyl) acetate boosts the sensory profile of (3-acetoxy-2,2-dimethyl-propyl) acetate.

Accordingly, the present invention relates to the use of (3-hydroxy-2,2-dimethyl-propyl) acetate for enhancing and/or modifying the aroma of (3-acetoxy-2,2-dimethyl-propyl) acetate. According to a preferred embodiment, the present invention relates to the use of (3-hydroxy-2,2-dimethyl-propyl) acetate for enhancing and/or modifying the olfactory impression, preferably the fragrance impression of (3-acetoxy-2,2-dimethyl-propyl) acetate.

In one embodiment of the invention (3-hydroxy-2,2-dimethyl-propyl) acetate is used to boost the fresh note of the aroma of (3-acetoxy-2,2-dimethyl-propyl) acetate. In one embodiment of the invention (3-hydroxy-2,2-dimethyl-propyl) acetate is used to impart a citrus note to the aroma of (3-acetoxy-2,2-dimethyl-propyl) acetate. In one embodiment of the invention (3-hydroxy-2,2-dimethyl-propyl) acetate is used to impart a berry note to the aroma of (3-acetoxy-2,2-dimethyl-propyl) acetate.

One embodiment of the present invention relates to the use of (3-acetoxy-2,2-dimethyl-propyl) acetate in combination with (3-hydroxy-2,2-dimethyl-propyl) acetate as an aroma chemical. A preferred embodiment relates to the use of (3-acetoxy-2,2-dimethyl-propyl) acetate in combination with (3-hydroxy-2,2-dimethyl-propyl) acetate as a fragrance.

One embodiment of the invention relates to the use of (3-acetoxy-2,2-dimethyl-propyl) acetate in combination with (3-hydroxy-2,2-dimethyl-propyl) acetate to impart a citrus-like note to a composition.

One embodiment of the invention relates to the use of (3-acetoxy-2,2-dimethyl-propyl) acetate in combination with (3-hydroxy-2,2-dimethyl-propyl) acetate to impart a berry note to a composition.

One embodiment of the invention is directed to the use of (3-acetoxy-2,2-dimethyl-propyl) acetate in combination with (3-hydroxy-2,2-dimethyl-propyl) acetate to impart a soft, fruity, gourmand, fresh and slightly citrus-like note to a composition.

It has surprisingly been found, that (3-acetoxy-2,2-dimethyl-propyl) acetate in combination with (3-hydroxy-2,2-dimethyl-propyl) acetate can boost the sensory properties of compositions comprising at least one aroma chemical (i), which is different from (3-hydroxy-2,2-dimethyl-propyl) acetate and (3-acetoxy-2,2-dimethyl-propyl) acetate.

The combination of (3-acetoxy-2,2-dimethyl-propyl) acetate and (3-hydroxy-2,2-dimethyl-propyl) acetate in particular, makes the sensory property of an aroma composition nicer and more concise and, optionally, adds a further aroma impression, preferably a further fragrance impression to the composition.

Accordingly, a further embodiment of the invention relates to the use of (3-acetoxy-2,2-dimethyl-propyl) acetate in combination with (3-hydroxy-2,2-dimethyl-propyl) acetate for enhancing and/or modifying the aroma (preferably the odor, more preferably the fragrance impression) of a composition, which further comprises at least one aroma chemical (i), which is different from (3-hydroxy-2,2-dimethyl-propyl) acetate and (3-acetoxy-2,2-dimethyl-propyl) acetate.

In preferred embodiments of the present invention, the combination of (3-acetoxy-2,2-dimethyl-propyl) acetate and (3-hydroxy-2,2-dimethyl-propyl) acetate is used in a composition selected from the group consisting of perfume compositions, body care compositions (including cosmetic compositions and products for oral and dental hygiene), hygiene articles, cleaning compositions (including dishwashing compositions), textile detergent compositions, compositions for scent dispensers, foods, food supplements, pharmaceutical compositions and crop protection compositions.

Furthermore, the combination of (3-acetoxy-2,2-dimethyl-propyl) acetate and (3-hydroxy-2,2-dimethyl-propyl) acetate can have further positive effects on the composition in which it is used. For example, the combination can enhance the overall performance of the composition into which it is incorporated, such as the stability, e.g. the formulation stability, the extendibility or the staying power of the composition.

The boosting can be achieved by varying the amount of (3-hydroxy-2,2-dimethyl-propyl) acetate and (3-acetoxy-2,2-dimethyl-propyl) acetate and/or the amount of (3-hydroxy-2,2-dimethyl-propyl) acetate based on the total amount of (3-hydroxy-2,2-dimethyl-propyl) acetate and (3-acetoxy-2,2-dimethyl-propyl) acetate.

Compositions

A further embodiment of the present invention relates to a composition comprising (3-acetoxy-2,2-dimethyl-propyl) acetate combined with (3-hydroxy-2,2-dimethyl-propyl) acetate and:

(i) at least one aroma chemical, or
(ii) at least one non-aroma chemical carrier, or
(iii) both of (i) and (ii).

Said composition is preferably an aroma chemical composition, more preferably a fragrance composition.

One embodiment of the invention is directed to a composition comprising (3-acetoxy-2,2-dimethyl-propyl) acetate combined with (3-hydroxy-2,2-dimethyl-propyl) acetate and at least one aroma chemical (i).

One embodiment of the invention is directed to a composition comprising (3-acetoxy-2,2-dimethyl-propyl) acetate combined with (3-hydroxy-2,2-dimethyl-propyl) acetate and at least one non-aroma chemical carrier (ii).

One embodiment of the invention is directed to a composition comprising (3-acetoxy-2,2-dimethyl-propyl) acetate combined with (3-hydroxy-2,2-dimethyl-propyl) acetate and (i) at least one aroma chemical and
(ii) at least one non-aroma chemical carrier.

The combination of (3-acetoxy-2,2-dimethyl-propyl) acetate and (3-hydroxy-2,2-dimethyl-propyl) acetate can preferably be used in aroma compositions. In preferred embodiments, the aroma composition is a fragrance composition, i.e. induces a pleasant odor.

The composition according to the invention can be selected from, but is not limited to, the group consisting of perfume compositions, body care compositions (including cosmetic compositions and products for oral and dental hygiene), hygiene articles, cleaning compositions (including dishwashing compositions), textile detergent compositions, compositions for scent dispensers, foods, food supplements, pharmaceutical compositions and crop protection compositions.

Compositions Comprising at Least One Aroma Chemical (i)

By virtue of the physical properties of (3-hydroxy-2,2-dimethyl-propyl) acetate and (3-acetoxy-2,2-dimethyl-propyl) acetate, combinations of said compounds have particularly good, virtually universal solvent properties for aroma chemicals and other customary ingredients in aroma compositions such as, in particular, fragrance compositions. Therefore, combinations of (3-acetoxy-2,2-dimethyl-propyl) acetate and (3-hydroxy-2,2-dimethyl-propyl) acetate are well combinable with aroma chemicals which are different from 3-acetoxy-2,2-dimethyl-propyl) acetate and (3-hydroxy-2,2-dimethyl-propyl) acetate, allowing, in particular, the creation of aroma compositions (preferably fragrance compositions) having novel advantageous sensory profiles. Especially, as already explained above, the combinations can boost the sensory profile of aroma chemicals (such as for example of fragrances) wherein said aroma chemicals are different from (3-hydroxy-2,2-dimethyl-propyl) acetate and (3-acetoxy-2,2-dimethyl-propyl) acetate.

The compositions of the invention can comprise at least one aroma chemical that is different from (3-hydroxy-2,2-dimethyl-propyl) acetate and (3-acetoxy-2,2-dimethyl-propyl) acetate. Said at least one aroma chemical can for example be one, preferably 2, 3, 4, 5, 6, 7, 8 or more aroma chemicals.

Said at least one aroma chemical can for example be one, preferably 2, 3, 4, 5, 6, 7, 8 or more aroma chemicals, selected from the group consisting of:

Geranyl acetate (3,7-Dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60 wt. %) (Hedione[9], Hedione HC[9]), 4,6,6,7,8,8-hexamethyl-1,3,4,6,7,8-hexahydro-cyclopenta[g]benzopyran (Galaxolid[3]), tetrahydrolinalool (3,7-dimethyloctan-3-ol), ethyllinalool, benzyl salicylate, 2-methyl-3-(4-tert-butylphenyl)propanal (Lysmeral[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl) butanal (Florhydral[2]), 2-methyl-3-(3,4-methylenedioxyphenyl)-propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70 wt. %) or more, 2,5,5-trimethyl-1,2,3,4,4a,5,6,7-octahydronaphthalen-2-ol (Ambrinol S[1]), 3-(4-tert-butylphenyl)-propanal (Bourgeonal[4]), ethyl 2-methylpentanoate (Manzanate[4]), ethoxymethoxycyclododecane (Amberwood[1]), 2,4-dimethyl-4,4a,5,9b-tetrahydroindeno[1,2-d][1,3]dioxine (Magnolan[1]), (2-tert-butylcyclohexyl) acetate (Verdox[3]) and 3-[5,5,6-trimethylbicyclo[2.2.1]hept-2-yl]cyclohexan-1-ol (Sandela[4]).

Within the context of the present invention, the aforementioned aroma chemical(s) are accordingly preferably combined with (3-acetoxy-2,2-dimethyl-propyl) acetate and (3-hydroxy-2,2-dimethyl-propyl) acetate as described above.

Where trade names are given above, these refer to the following sources:

[1] trade name of Symrise GmbH, Germany;
[2] trade name of BASF SE;
[3] trade name of International Flavors & Fragrances Inc., USA;
[4] Givaudan AG, Switzerland;
[9] trade name of Firmenich S.A., Switzerland;
[10] trade name of PFW Aroma Chemicals B.V., the Netherlands.

A further embodiment of the invention relates to a composition comprising (3-acetoxy-2,2-dimethyl-propyl) acetate combined with (3-hydroxy-2,2-dimethyl-propyl) acetate and at least one aroma chemical selected from the group consisting of methyl benzoate, benzyl acetate, geranyl acetate, 2-isobutyl-4-methyltetrahydro-2H-pyran-4-ol and linalool.

A further embodiment of the invention relates to a composition comprising (3-acetoxy-2,2-dimethyl-propyl) acetate combined with (3-hydroxy-2,2-dimethyl-propyl) acetate and 2-isobutyl-4-methyltetrahydro-2H-pyran-4-ol.

A further embodiment of the invention relates to a composition comprising (3-acetoxy-2,2-dimethyl-propyl) acetate combined with (3-hydroxy-2,2-dimethyl-propyl) acetate and methyl benzoate.

Further aroma chemicals with which the combination of (3-acetoxy-2,2-dimethyl-propyl) acetate and (3-hydroxy-2,2-dimethyl-propyl) acetate can be combined to give a composition according to the invention can be found, e.g., in S. Arctander, Perfume and Flavor Chemicals, Vol. I and II, Montclair, N.J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil;

citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; *Eucalyptus citriodora* oil; *Eucalyptus* oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; *Litsea cubeba* oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethylacetals of geranial, neral, 7-hydroxy-3,7-dimethyloctanal; the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3- dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyl-dodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; alpha-rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclo-hexadecen-1-one; 7-cyclohexadecen-1-one; (7/8)-cyclohexadecen-1-one; 9-cyclo-heptadecen-1-one; cyclopentadecanone; cyclohexadecanone:

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclo-hexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylaceto-phenone; 4-phenyl-2-butanone; 4-(4-hydroxyphenyl)-2-butanone; 1-(2-naphthalenyl)-ethanone; 2-benzofuranylethanone; (3-methyl-2-benzofuranyl)ethanone; benzo-phenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropyl-pyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Advantageous are combinations with aroma chemicals with a sweet note, such as ethylvanillin, vanillin, 2,5-dimethyl-4-hydroxy-2H-furan-3-one (furaneol) or 3-hydroxy-2-methyl-4H-pyran-4-one (maltol). In these embodiments the sweet note is boosted by (3-acetoxy-2,2-dimethyl-propyl) acetate combined with (3-hydroxy-2,2-dimethyl-propyl) acetate.

Accordingly, a further embodiment of the invention relates to a composition comprising (3-acetoxy-2,2-dimethyl-propyl) acetate combined with (3-hydroxy-2,2-dimethyl-propyl) acetate and at least one aroma chemical selected from the group consisting of ethylvanillin, vanillin, 2,5-dimethyl-4-hydroxy-2H-furan-3-one (furaneol) or 3-hydroxy-2-methyl-4H-pyran-4-one (maltol).

Compositions Comprising at Least One Non-Aroma Chemical Carrier (ii)

A further embodiment of the invention is directed to a composition comprising (3-acetoxy-2,2-dimethyl-propyl) acetate combined with (3-hydroxy-2,2-dimethyl-propyl) acetate and at least one non-aroma chemical carrier (ii). Said non-aroma chemical carrier(s) is/are preferably different from toluene.

The at least one non-aroma chemical carrier (ii) can be a compound, a mixture of compounds or other additives, which has/have no or no noteworthy sensory properties. The non-aroma chemical carrier (ii) can serve for the dilution and/or the fixing of 3-acetoxy-2,2-dimethyl-propyl) acetate and (3-hydroxy-2,2-dimethyl-propyl) acetate and—optionally the at least one aroma chemical (i), as defined above, if comprised in the composition.

A further embodiment of the invention is directed to a composition comprising (3-acetoxy-2,2-dimethyl-propyl) acetate combined with (3-hydroxy-2,2-dimethyl-propyl) acetate and at least one non-aroma chemical carrier selected from the group consisting of surfactants, oil components and solvents. Said non-aroma chemical carrier(s) is/are preferably different from toluene.

According to preferred embodiments of the present invention, said non-aroma chemical carrier(s) is/are selected from surfactants, oil components and solvents listed below.

One embodiment of the invention is directed to a composition comprising acetoxy-2,2-dimethyl-propyl) acetate combined with (3-hydroxy-2,2-dimethyl-propyl) acetate as described herein and at least one solvent. Said solvent(s) is/are preferably different from toluene.

In the context of the present invention, a "solvent" serves for the dilution of (3-hydroxy-2,2-dimethyl-propyl) acetate and/or (3-acetoxy-2,2-dimethyl-propyl) acetate to be used according to the invention without having its own aroma.

The one or more solvent(s) can be present in the composition in amount of 0.01 to 99 wt. % based on the composition. In a preferred embodiment of the invention, the composition comprises 0.1 to 90 wt. %, preferably 0.5 to 80 wt. % of solvent(s) based on the total weight of the composition. The amount of solvent(s) can be chosen depending on the composition. In one embodiment of the invention, the composition comprises 0.05 to 10 wt. %, preferably 0.1 to 5 wt. %, more preferably 0.2 to 3 wt. % based on the total weight of the composition. In one embodiment of the invention, the composition comprises 20 to 70 wt. %, preferably 25 to 50 wt. % of solvent(s) based on the total weight of the composition.

Preferred solvents are ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), 1-Methoxypropan-2-ol and benzyl benzoate (BB).

Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further embodiment, the combination of (3-acetoxy-2,2-dimethyl-propyl) acetate and (3-hydroxy-2,2-dimethyl-propyl) acetate is used according to the present invention in surfactant-containing compositions. Due to its characteristic fragrance property, the combination can especially be used to provide an odor, preferably a fragrance impression to surfactant-containing compositions such as, for example, cleaners (in particular laundry care products and all-purpose cleaners).

One embodiment of the invention is therefore directed to a composition comprising (3-acetoxy-2,2-dimethyl-propyl) acetate combined with (3-hydroxy-2,2-dimethyl-propyl) acetate and at least one surfactant.

The surfactant(s) may be selected from anionic, nonionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in an amount of 0 to 40 wt. %, preferably 0 to 20 wt. %, more preferably 0.1 to 15 wt. %, and particularly 0.1 to 10 wt. %, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_8$ to $C_{18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalk-ylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12}$-$C_{18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trim ethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising (3-acetoxy-2,2-dimethyl-propyl) acetate combined with (3-hydroxy-2,2-dimethyl-propyl) acetate and at least one oil component.

The oil components are typically present in an amount of 0.1 to 80 wt. %, preferably 0.5 to 70 wt. %, more preferably 1 to 60 wt. %, even more preferably 1 to 50 wt. %, in particular 1 to 40 wt. %, more particularly 5 to 25 wt. % and specifically 5 to 15 wt. % based on the total weight of the composition.

The oil components may be selected, for example, from Guerbet alcohols based on fatty alcohols containing 6 to 18, preferably 8 to 10, carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$ alkyl-hydroxycarboxylic acids with linear or branched $C_6$-$C_{22}$ fatty alcohols, more especially dioctyl malate, esters of linear and/or branched fatty acids with polyhydric alcohols (for example propylene glycol, dimer dial or trimer triol), triglycerides based on $C_6$-$C_{10}$ fatty acids, liquid mono-, di- and triglyceride mixtures based on $C_6$-$C_{18}$ fatty acids, esters of $C_6$-$C_{22}$ fatty alcohols and/or Guerbet alcohols with aromatic carboxylic acids, more particularly benzoic acid, esters of dicarboxylic acids with polyols containing 2 to 10 car-bon atoms and 2 to 6 hydroxyl groups, vegetable oils, branched primary alcohols, substituted cyclohexanes, linear and branched $C_6$-$C_{22}$ fatty alcohol carbonates such as, for example, dicaprylyl carbonate (Cetiol® CC), Guerbet carbonates based on fatty alcohols containing 6 to 18, preferably 8 to 10, carbon atoms, esters of benzoic acid with linear and/or branched $C_6$ to $C_{22}$ alcohols (for example Finsolv® TN), linear or branched, symmetrical or nonsymmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

Combinations of (3-acetoxy-2,2-dimethyl-propyl) acetate and (3-hydroxy-2,2-dimethyl-propyl) acetate as described herein can be used in a wide range of compositions, preferably in aroma compositions, more preferably in fragrance compositions. The olfactory properties and the substance properties (such as solubility in customary solvents and compatibility with further customary constituents of such compositions) of the combinations and their components (3-hydroxy-2,2-dimethyl-propyl) acetate and (3-acetoxy-2,2-dimethyl-propyl) acetate underline the particular suitability of the combinations for the stated use purposes and compositions.

Suitable compositions are for example perfume compositions, body care compositions (including cosmetic compositions and products for oral and dental hygiene), hygiene articles, cleaning compositions (including dishwashing compositions), textile detergent compositions, compositions for scent dispensers, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Parfum.

Body care compositions include cosmetic compositions and products for oral and dental hygiene, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hairsprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eye-shadows, nail varnishes, make-ups, lipsticks and mascara, and products for oral and dental hygiene, such as toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing compositions both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, anti-dandruff agents, anti-inflammatory agents, irritation-preventing agents, irritation-alleviating agents, antimicrobial agents, antioxidants, astringents, sweat-inhibiting agents, antiseptics, anti-statics, binders, buffers, carrier materials, chelating agents, cell stimulants, cleaning agents, care agents, hair removal agents, surface-active substances, deodorizing agents, antiperspirants, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, waxes, fats, phospholipids, saturated fatty acids, mono- or polyunsaturated fatty acids, α-hydroxy acids, polyhydroxy fatty acids, liquefiers, dyes, color-protection agents, pigments, anti-corrosives, polyols, electrolytes, or silicone derivatives.

Preparation of Compositions (3-acetoxy-2,2-dimethyl-propyl) acetate in combination with (3-hydroxy-2,2-dimethyl-propyl) acetate as described herein may be employed in compositions simply by directly mixing (3-acetoxy-2,2-dimethyl-propyl) acetate and (3-hydroxy-2,2-dimethyl-propyl) acetate with the composition. (3-acetoxy-2,2-dimethyl-propyl) acetate and (3-hydroxy-2,2-dimethyl-propyl) acetate can be incorporated into the composition in the form of a mixture or composition comprising these two compounds (and thus concurrently) or separately (sequentially or concurrently).

In an further embodiment, (3-acetoxy-2,2-dimethyl-propyl) acetate and (3-hydroxy-2,2-dimethyl-propyl) acetate may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or may be chemically bonded to substrates, which are adapted to release the (3-acetoxy-2,2-dimethyl-propyl) acetate and (3-hydroxy-2,2-dimethyl-propyl) acetate upon application of an external stimulus such as light, enzyme, or the like, and then mixed with the composition.

The combination of (3-acetoxy-2,2-dimethyl-propyl) acetate and (3-hydroxy-2,2-dimethyl-propyl) acetate and compositions comprising these compounds according to the present invention can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising (3-acetoxy-2,2-dimethyl-propyl) acetate and (3-hydroxy-2,2-dimethyl-propyl) acetate, or a composition of the present invention described herein, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting (3-acetoxy-2,2-dimethyl-propyl) acetate and (3-hydroxy-2,2-dimethyl-propyl) acetate, or a composition of the present invention described herein with a suitable wax-like substance and by extrusion with subsequent solidification, optionally in a suitable solvent, e.g. isopropanol.

A further embodiment of the invention is directed to a method of preparing a composition, preferably an aroma composition, preferably a fragrance composition, comprising incorporating (3-acetoxy-2,2-dimethyl-propyl) acetate and (3-hydroxy-2,2-dimethyl-propyl) acetate, into a composition. The composition prepared by said method can be an aroma composition, preferably a fragrance composition.

For example, the method can be carried out by mixing (3-acetoxy-2,2-dimethyl-propyl) acetate and (3-hydroxy-2, 2-dimethyl-propyl) acetate and:
(i) at least one aroma chemical, or
(ii) at least one non-aroma chemical carrier, or
(iii) both of (i) and (ii).

Said at least one aroma chemical is different from (3-hydroxy-2,2-dimethyl-propyl) acetate and (3-acetoxy-2,2-dimethyl-propyl) acetate. The composition prepared by the method of the invention is preferably an aroma chemical composition.

The invention is also directed to a method for enhancing and/or modifying the aroma of a composition, preferably of a fragrance composition, wherein the method comprises incorporating (3-acetoxy-2,2-dimethyl-propyl) acetate and (3-hydroxy-2,2-dimethyl-propyl) acetate, into an composition, preferably into a fragrance composition.

In particular, the invention is directed to a method of preparing a perfume composition, body care composition, hygiene article, cleaning composition, textile detergent composition, composition for scent dispensers, food, food supplement, pharmaceutical composition or crop protection composition, comprising including (3-acetoxy-2,2-dimethyl-propyl) acetate and (3-hydroxy-2,2-dimethyl-propyl) acetate in a perfume composition, body care composition, hygiene article, cleaning composition, textile detergent composition, composition for scent dispensers, food, food supplement, pharmaceutical composition or crop protection composition.

In the above-mentioned methods, (3-acetoxy-2,2-dimethyl-propyl) acetate and (3-hydroxy-2,2-dimethyl-propyl) acetate can be incorporated into the composition in the form of a mixture or composition comprising these two compounds (and thus concurrently) or separately (sequentially or concurrently).

Amount(s)

Generally, the amount of the combination of (3-acetoxy-2,2-dimethyl-propyl) acetate and (3-hydroxy-2,2-dimethyl-propyl) acetate in the compositions, methods and uses according to the present invention is typically adapted to the particular intended use or the intended application and can, thus, vary over a wide range. As a rule, the customary standard commercial amounts for aroma chemicals, preferably for scents are used.

The compositions according to the invention can comprise the combination of (3-acetoxy-2,2-dimethyl-propyl) acetate and (3-hydroxy-2,2-dimethyl-propyl) acetate in an amount of 0.001 to 99.9 wt. %, based on the total weight of the composition.

The compositions of the invention can comprise the combination of (3-acetoxy-2,2-dimethyl-propyl) acetate and (3-hydroxy-2,2-dimethyl-propyl) acetate in an amount of 0.001 to 99.5 wt. %, preferably 50 to 99 wt. %, in particular of 80 to 95 wt. %, more particularly of 90 to 95 wt. %, based on the total weight of the composition.

The compositions of the invention can comprise the combination of (3-acetoxy-2,2-dimethyl-propyl) acetate and (3-hydroxy-2,2-dimethyl-propyl) acetate in an amount of 0.005 to 80 wt. %, preferably an amount of 0.1 to 30 wt. %, more preferably from 1 to 20 wt. %, and in particular an amount of 5 to 15 wt. %, based on the total weight of the composition.

The compositions of the invention can comprise the combination of (3-acetoxy-2,2-dimethyl-propyl) acetate and (3-hydroxy-2,2-dimethyl-propyl) acetate described herein in an amount of 0.001 to 20 wt. %, preferably an amount of 0.005 to 6 wt. %, more preferably from 0.05 to 4 wt. %, and in particular from 0.1 to 3 wt. %, based on the total weight of the composition.

Generally, the amount of (3-hydroxy-2,2-dimethyl-propyl) acetate in relation to the amount of (3-hydroxy-2,2-dimethyl-propyl) acetate and (3-acetoxy-2,2-dimethyl-propyl) acetate in the compositions, uses and methods according to the present invention is typically adapted to the particular intended use or the intended application and can, thus, vary over a wide range.

In the compositions, uses and methods of the present invention (3-hydroxy-2,2-dimethyl-propyl) acetate is preferably used in an amount of at least 0.001 wt. %, more preferably of at least 0.005 wt. %, preferably of at least 0.01 wt. %, more preferably of at least 0.05 wt. %, more preferably of at least 0.06 wt. % more preferably of at least 0.07 wt. % more preferably of at least 0.1 wt. %, more preferably of at least 0.25 wt. %, more preferably of at least 0.5 wt. %, more preferably of at least 1 wt. % of (3-hydroxy-2,2-dimethyl-propyl) acetate based on the total weight of (3-hydroxy-2,2-dimethyl-propyl) acetate and (3-acetoxy-2,2-dimethyl-propyl) acetate.

It is within the scope of the present invention, that (3-hydroxy-2,2-dimethyl-propyl) acetate is used in an amount of at least 1.1 wt. %, preferably of at least 1.2 wt. %, more preferably of at least 1.5 wt. %, more preferably of at least 2 wt. %, more preferably of at least 5 wt. % of (3-hydroxy-2,2-dimethyl-propyl) acetate based on the total weight of (3-hydroxy-2,2-dimethyl-propyl) acetate and (3-acetoxy-2,2-dimethyl-propyl) acetate.

In the compositions, uses and methods of the present invention (3-hydroxy-2,2-dimethyl-propyl) acetate is preferably used in an amount of 50 wt. % or less than 50 wt. %, preferably of 25 wt. % or less than 25 wt. %, preferably of 20 wt. % or less than 20 wt. %, more preferably of 15 wt. % or less than 15 wt. %, more preferably of 10 wt. % or less than 10 wt. % of (3-hydroxy-2,2-dimethyl-propyl) acetate based on the total weight of (3-hydroxy-2,2-dimethyl-propyl) acetate and (3-acetoxy-2,2-dimethyl-propyl) acetate.

In the compositions, uses and methods of the present invention (3-hydroxy-2,2-dimethyl-propyl) acetate is preferably used in an amount of 0.001 wt. % to 50 wt. %, preferably of 0.01 wt. % to 20 wt. %, more preferably of 0.1 wt. % to 15 wt. % of (3-hydroxy-2,2-dimethyl-propyl) acetate based on the total weight of (3-hydroxy-2,2-dimethyl-propyl) acetate and (3-acetoxy-2,2-dimethyl-propyl) acetate.

Preparation of (3-hydroxy-2,2-dimethyl-propyl) acetate and (3-acetoxy-2,2-dimethyl-propyl) acetate (3-hydroxy-2,2-dimethyl-propyl) acetate and (3-acetoxy-2,2-dimethyl-propyl) acetate can be prepared by standard methods of organic chemistry and by methods as described in the art. To be more precise, (3-hydroxy-2,2-dimethyl-propyl) acetate and (3-acetoxy-2,2-dimethyl-propyl) acetate can be prepared by standard methods for preparing 1,3-diol-based esters, for examples as described in WO 98/32728 and WO 2016/118882.

(3-hydroxy-2,2-dimethyl-propyl) acetate and (3-acetoxy-2,2-dimethyl-propyl) acetate are esters which can be prepared acetylation of the respective alcohol (2,2-dimethyl-propane-1,3-diol, also termed neopentyl glycol), i.e. esterification of 2,2-dimethylpropane-1,3-diol by reaction with, e.g. acetic acid, acetic anhydride or an acetyl halogenide (such as, e.g., acetyl bromide or acetyl chloride). Thus, (3-hydroxy-2,2-dimethyl-propyl) acetate and (3-acetoxy-2,2-dimethyl-propyl) acetate can be prepared by reacting 2,2-dimethylpropane-1,3-diol with (i) acetic acid or (ii) acetic anhydride or (iii) acetyl halogenide or a mixture of (i)-(iii). Said reaction is typically performed in the presence of an esterification catalyst or a base.

Suitable esterification catalysts and bases that can be applied in this reaction are well known to the skilled person. Suitable esterification catalysts are, for example, mineral acids (e.g., sulfuric acid, hydrochloric acid or phosphoric acid) or organic sulfonic acids (e.g., methane sulfonic acid or para-toluene sulfonic acid).

Bases are in particular used in acetylations with acetic anhydride or acetyl halogenide (such as, e.g., acetyl bromide or acetyl chloride). Suitable bases are, for example, tertiary amines (e.g., trimethylamine, triethylamine, tripropylamine, ethyldiisopropylamine and the like), or basic N-heterocycles (e.g., morpholine, pyridine, lutidine, DMAP, DABCO, DBU, DBN or imidazoles).

Suitable reaction conditions for such preparation of (3-hydroxy-2,2-dimethyl-propyl) acetate and (3-acetoxy-2,2-dimethyl-propyl) acetate are well known to the skilled person.

For the preparation of the monoester (3-hydroxy-2,2-dimethyl-propyl) acetate, 2,2-dimethylpropane-1,3-diol is typically reacted with sub-equimolar up to equimolar amounts, e.g. 0.7, 0.8, 0.9, or 1.0 equivalents of acetic acid, acetic anhydride, acetyl halogenide or a mixture thereof.

For the preparation of the diester (3-acetoxy-2,2-dimethyl-propyl) acetate, 2,2-dimethylpropane-1,3-diol is typically reacted with at least two equivalents, e.g. 2.0, 2.1, 2.5 or 3.0 equivalents, of acetic acid, acetic anhydride, acetyl halogenide or a mixture thereof.

Typically, the raw product obtained from the acetylation is subsequently purified to remove unwanted by-products and/or impurities, e.g. residual starting material and/or catalyst. Generally, purification is performed using common purification methods such as, e.g., crystallization, distillation or chromatographic methods, for example column chromatography or high-performance liquid chromatography. If the raw product contains only minor amounts of impurities and by-products it can be purified by a simple extractive workup.

Further embodiments of the present invention relate to:
the use of (3-hydroxy-2,2-dimethyl-propyl) acetate for enhancing and/or modifying the aroma of an aroma chemical composition;
a composition comprising (3-hydroxy-2,2-dimethyl-propyl) acetate and:
(i) at least one aroma chemical (that is different from (3-hydroxy-2,2-dimethyl-propyl) acetate), or
(ii) at least one non-aroma chemical carrier, or
both of (i) and (ii);
a method of preparing a composition, the method comprising mixing (3-hydroxy-2,2-dimethyl-propyl) acetate with other ingredients such as, e.g., at least one aroma chemical (that is different from (3-hydroxy-2,2-dimethyl-propyl) acetate) and/or at least one non-aroma chemical carrier so as to obtain the composition;
a method of enhancing and/or modifying the aroma of an composition, the method comprising incorporating (3-hydroxy-2,2-dimethyl-propyl) acetate into a composition.
and other embodiments of the methods and uses described herein, wherein (3-hydroxy-2,2-dimethyl-propyl) acetate is used instead of a combination of (3-acetoxy-2,2-dimethyl-propyl) acetate and (3-hydroxy-2,2-dimethyl-propyl) acetate in an analogous manner.

A further embodiment of the present invention relates to the use of (3-hydroxy-2,2-dimethyl-propyl) acetate in combination with (3-acetoxy-2,2-dimethyl-propyl) acetate as a solvent for one or more aroma chemicals. Said one or more aroma chemicals are different from (3-acetoxy-2,2-dimethyl-propyl) acetate and (3-hydroxy-2,2-dimethyl-propyl) acetate.

The following examples serve as further illustration of the invention.

Examples

1. Preparation of (3-hydroxy-2,2-dimethyl-propyl) acetate

A solution of 2,2-dimethylpropane-1,3-diol (343.1 g) in tetrahydrofuran (150 g) was provided at 65° C. Acetic anhydride (338.9 g) was added to said solution drop by drop within 30 min. After 2.5 h the mixture was left to cool to room temperature and the solvent was removed by means of a rotary evaporator. The residue was redissolved in toluene and extracted several times with water to remove residual 2,2-dimethyl-propane-1,3-diol. The solvent of the organic phase was then removed by means of a rotary evaporator. Part of the residue was transferred into a large excess of water and was extracted several times with small portions of hexane to remove (3-acetoxy-2,2-dimethyl-propyl) acetate. Finally, the aqueous phase was extracted with 2-methoxy-2-methylpropane (MTBE). Then, the solvent was removed and (3-hydroxy-2,2-dimethyl-propyl) acetate of >99% purity was obtained.

$^{13}$C-NMR (125 MHz, CDCl$_3$): δ=171.5, 69.2, 67.7, 35.8, 21.1 (2C), 20.5 ppm. $^{1}$H-NMR (500 MHz, CDCl3): δ=3.72 (s, 2H), 3.42 (br s, OH), 3.14 (s, 2H), 1.89 (s, 3H), 0.73 (s, 6H) ppm.

2. Preparation of (3-acetoxy-2,2-dimethyl-propyl) acetate

Acetic anhydride (4019 g) was provided in a reactor under reflux at about 140° C. 2,2-Dimethylpropane-1,3-diol (2000 g) was melted at about 150° C. and dosed to the reactor containing acetic anhydride within 90 min under significant generation of heat. Subsequent to said addition of the 2,2-dimethylpropane-1,3-diol, the mixture was stirred for 30 min and then left to cool to room temperature. The crude product (5992 g) was processed by an agitated thin-film evaporator (8000-4000 Pa, 90-110° C.) and subsequently purified by a second agitated thin-film evaporation (2000-2500 Pa, 120° C.). Fractional distillation gave (3-acetoxy-2,2-dimethyl-propyl) acetate of >99% purity.

$^{13}$C-NMR (125 MHz, CDCl$_3$): d=170.8 (2C), 69.1 (2C), 34.6, 21.7 (2C), 20.7 (2C) ppm.

$^1$H-NMR (500 MHz, CDCl$_3$): δ=3.69 (s, 4H), 1.87 (s, 6H), 0.78 (s, 6H) ppm.

3. Olfactory Tests

The quality and intensity of the odor of mixtures of (3-hydroxy-2,2-dimethyl-propyl) acetate and (3-acetoxy-2,2-dimethyl-propyl) acetate was assessed by performing scent strip tests.

For this purpose, (3-acetoxy-2,2-dimethyl-propyl) acetate was mixed with certain amounts of (3-hydroxy-2,2-dimethyl-propyl) acetate. Strips of absorbent paper were dipped into the mixture to be tested. The scent impression was olfactively evaluated by a panel of 3 trained perfumers.

The results of the scent test are summarized in table 1.

TABLE 1

Evaluation of odor

| Example no. | (3-hydroxy-2,2-dimethyl-propyl) acetate [wt. %]* | Odor Description |
|---|---|---|
| 1.1 | 0.0 wt. % | as described in WO 2016/118882—soft, fruity, gourmand, fresh |
| 1.2 | 0.1 wt. % | increased niceness and conciseness compared to 1.1, especially with regard to the fresh note; and an extra lift that adds a slightly citrus-like note |
| 1.3 | 3.0 wt. % | improves the niceness and conciseness of 1.1, especially with regard to the fresh note and adds a natural berry fruitiness |

*Amount of (3-hydroxy-2,2-dimethyl-propyl) acetate in wt. % relative to the total weight of the mixture of (3-hydroxy-2,2-dimethyl-propyl) acetate and (3-acetoxy-2,2-dimethyl-propyl) acetate

2. Advantageous Fragrance Compositions

The mixtures of examples 1.2 and 1.3 were formulated in the compositions according to tables 2 and 3. The amounts given in tables 2 and 3 are weight units in grams.

TABLE 2

Fragrance compositions 1A and 1B

| | 1A | 1B |
|---|---|---|
| Lactone C10 gamma (5-hexyloxolan-2-one) | 2 | 2 |
| Bourgeonal (3-(4-tert-butylphenyl)propanal) | 2 | 2 |
| Citronellol | 3 | 3 |
| Aldehyde C-14 (5-heptyloxolan-2-one) | 3 | 3 |
| Allyl heptylate | 4 | 4 |
| Amber core (1-(2-tert-butylcyclohexyl)oxybutan-2-ol) | 4 | 4 |
| Ethyl-2-methyl butyrate | 4 | 4 |
| Geranyl acetate | 5 | 5 |
| Helional (3-(1,3-benzodioxol-5-yl)-2-methylpropanal) | 10 | 10 |
| Manzanate (ethyl 2-methylpentanoate) | 10 | 10 |
| Amberwood (ethoxymethoxycyclododecane) | 10 | 10 |
| Hexyl acetate | 11 | 11 |
| Benzyl salicylate | 12 | 12 |
| Magnolan (2,4-dimethyl-4,4a,5,9b-tetrahydroindeno[1,2-d][1,3]dioxine) | 15 | 15 |
| Verdox (2-tert-butylcyclohexyl) acetate) | 25 | 25 |
| Bergamot oil bergaptene free | 25 | 25 |
| Linalol | 30 | 30 |
| Dipropylene glycol | 45 | 45 |
| Iso E Super (Tetramethyl acetyloctahydronaphthalenes) | 110 | 110 |
| Pyranol (4-methyl-2-(2-methylpropyl)oxan-4-ol) | 170 | 170 |
| Hedione (methyl 3-oxo-2-pentylcyclopentaneacetate) | 200 | 200 |
| Galaxolide 50% IPM (1,3,4,6,7,8-hexahydro-4,6,6,7,8,8-hexamethylcyclopenta(g)-2-benzopyran 50% in isopropyl myristate) | 300 | 300 |
| Mixture of example 1.2 | 25 | 50 |
| | 1025 | 1050 |

TABLE 3

Fragrance compositions 2A and 2B

| | 2A | 2B |
|---|---|---|
| Raspberry ketone (4-(4-hydroxyphenyl)butan-2-one) | 4 | 4 |
| Vanitrope (2-ethoxy-5-prop-1-enylphenol) | 6 | 6 |
| Cyclamen aldehyde (at least 90% 2-methyl-3-(p-isopropylphenyl)-propionaldehyde; secondary component: 5% 3-(p-cumenyl)-2-methylpropionic acid) | 10 | 10 |
| Bicyclononalactone (3,4,4a,5,6,7,8,8a-octahydrochromen-2-one) | 10 | 10 |
| Aldehyde C-14 (5-heptyloxolan-2-one) | 14 | 14 |
| Ethylvanillin (3-ethoxy-4-hydroxybenzaldehyde) | 16 | 16 |
| Heliotropine (1,3-benzodioxole-5- | 20 | 20 |

TABLE 3-continued

Fragrance compositions 2A and 2B

| | 2A | 2B |
|---|---|---|
| carbaldehyde) | | |
| Iso E Super (tetramethyl acetyloctahydronaphthalenes) | 20 | 20 |
| Sandela (3-[5,5,6-trimethylbicyclo[2.2.1]hept-2-yl]cyclohexan-1-ol) | 30 | 30 |
| Vanillin isobutyrate ((4-formyl-2-methoxyphenyl) 2-methylpropanoate) | 40 | 40 |
| Aldehyde C-18 (5-pentyloxolan-2-one) | 50 | 50 |
| Benzyl salicylate | 60 | 60 |
| Hexyl cinnamic aldehyde (2-(phenylmethylidene)octanal) | 70 | 70 |
| Hedione (methyl 3-oxo-2-pentylcyclopentaneacetate) | 130 | 130 |
| Pyranol (4-methyl-2-(2-methylpropyl)oxan-4-ol) | 150 | 150 |
| Ethylene brassylate (1,4-dioxacycloheptadecane-5,17-dione) | 170 | 170 |
| Galaxolide 50% IPM (1,3,4,6,7,8-hexahydro-4,6,6,7,8,8-hexamethylcyclopenta(g)-2-benzopyran 50% in isopropyl myristate) | 200 | 200 |
| Mixture of example 1.2 | 100 | 200 |
| | 1100 | 1200 |

Fragrance composition 3 corresponds to fragrance composition 1A, where the mixture of example 1.2 is replaced by the same amount of the mixture of example 1.3.

Fragrance composition 4 corresponds to fragrance composition 2A, where the mixture of example 1.2 is replaced by the same amount of the mixture of example 1.3.

Fragrance composition 5 corresponds to fragrance composition 1B, where the mixture of example 1.2 is replaced by the same amount of the mixture of example 1.3.

Fragrance composition 6 corresponds to fragrance composition 2B, where the mixture of example 1.2 is replaced by the same amount of the mixture of example 1.3.

The invention claimed is:

1. A method for enhancing and/or modifying aroma of (3-acetoxy-2,2-dimethyl-propyl) acetate comprising adding (3-hydroxy-2,2-dimethyl-propyl) acetate to the (3-acetoxy-2,2-dimethyl-propyl) acetate in an amount of 0.01 wt. % to 20 wt. % based on the total weight of (3-hydroxy-2,2-dimethyl-propyl) acetate and (3-acetoxy-2,2-dimethyl-propyl) acetate.

2. The method according to claim 1, wherein (3-hydroxy-2,2-dimethyl-propyl) acetate is used for enhancing and/or modifying the fragrance impression of (3-acetoxy-2,2-dimethyl-propyl) acetate.

3. A method of providing an aroma to a composition, comprising incorporating (3-acetoxy-2,2-dimethyl-propyl) acetate in combination with (3-hydroxy-2,2-dimethyl-propyl) acetate as an aroma chemical into the composition, where (3-hydroxy-2,2-dimethyl-propyl) acetate is incorporated in an amount of 0.01 wt. % to 20 wt. % based on the total weight of (3-hydroxy-2,2-dimethyl-propyl) acetate and (3-acetoxy-2,2-dimthyl-propyl) acetate.

4. A method for enhancing and/or modifying the aroma of a composition, comprising adding (3-acetoxy-2,2-dimethyl-propyl) acetate in combination with (3-hydroxy-2,2-dimethyl-propyl) acetate, wherein the composition comprises at least one aroma chemical (i), which is different from (3-hydroxy-2,2-dimethyl-propyl) acetate and (3-acetoxy-2,2-dimethyl-propyl) acetate; where (3-hydroxy-2,2-dimethyl-propyl) acetate is added in an amount of 0.01 wt. % to 20 wt. %, based on the total weight of (3-hydroxy-2,2-dimethyl-propyl) acetate and (3-acetoxy-2,2-dimethyl-propyl) acetate.

5. The method according to claim 4, wherein (3-acetoxy-2,2-dimethyl-propyl) acetate and 3-hydroxy-2,2-dimethyl-propyl) acetate are used for enhancing and/or modifying the fragrance impression of the composition.

6. The method according to claim 4, wherein the composition selected from the group consisting of perfume compositions, body care compositions, hygiene articles, cleaning compositions, textile detergent compositions, compositions for scent dispensers, foods, food supplements, pharmaceutical compositions and crop protection compositions.

7. The method according to claim 1, wherein (3-hydroxy-2,2-dimethyl-propyl) acetate is used in an amount of 0.01 wt. % to 15 wt. % of (3-hydroxy-2,2-dimethyl-propyl) acetate based on the total weight of (3-hydroxy-2,2-dimethyl-propyl) acetate and (3-acetoxy-2,2-dimethyl-propyl) acetate.

8. Composition comprising (3-acetoxy-2,2-dimethyl-propyl) acetate combined with (3-hydroxy-2,2-dimethyl-propyl) acetate, where (3-hydroxy-2,2-dimethyl-propyl) acetate is present in an amount of 0.01 wt. % to 20 wt. %, based on the total weight of (3-hydroxy-2,2-dimethyl-propyl) acetate and (3-acetoxy-2,2-dimethyl-propyl) acetate, and:
(i) at least one aroma chemical which is different from (3-hydroxy-2,2-dimethyl-propyl) acetate and (3-acetoxy-2,2-dimethyl-propyl) acetate, or
(ii) at least one non-aroma chemical carrier, or
(iii) both of (i) and (ii);
wherein the composition is selected from the group consisting of perfume compositions, body care compositions, hygiene articles, cleaning compositions, textile detergent compositions, compositions for scent dispensers, foods, food supplements, pharmaceutical compositions and crop protection compositions.

9. The composition according to claim 8 which is an aroma composition.

10. The composition according to claim 9 which is a fragrance composition.

11. The composition according to claim 8, wherein (3-hydroxy-2,2-dimethyl-propyl) acetate is used in an amount of 0.01 wt. % to 15 wt. % of (3-hydroxy-2,2-dimethyl-propyl) acetate based on the total weight of (3-hydroxy-2,2-dimethyl-propyl) acetate and (3-acetoxy-2,2-dimethyl-propyl) acetate.

12. Composition comprising (3-acetoxy-2,2-dimethyl-propyl) acetate combined with (3-hydroxy-2,2-dimethyl-propyl) acetate, where (3-hydroxy-2,2-dimethyl-propyl) acetate is present in an amount of 0.01 wt. % to 20 wt. %, based on the total weight of (3-hydroxy-2,2-dimethyl-propyl) acetate and (3-acetoxy-2,2-dimethyl-propyl) acetate, and:
(i) at least one aroma chemical which is different from (3-hydroxy-2,2-dimethyl-propyl) acetate and (3-acetoxy-2,2-dimethyl-propyl) acetate, and
(ii) optionally at least one non-aroma chemical carrier;
wherein the at least one aroma chemical (i) which is different from (3-hydroxy-2,2-dimethyl-propyl) acetate and (3-acetoxy-2,2-dimethyl-propyl) acetate is selected from the group consisting of:
geranyl acetate (3,7-Dimethyl-2,6 octadien-1yl acetate), alpha-hexylcinnamaldehyde, 2-phenoxyethyl isobutyrate (Phenirat), dihydromyrcenol (2,6-dimethyl-7-octen-2-ol), methyl dihydrojasmonate (Hedione, Hedione HC), 4,6,6,7,8,8-hexamethyl-1,3,4,6,7,8-hexahydro-cyclopenta[g]benzopyran (Galaxolid), tetrahydrolinalool (3,7-dimethyloctan-3-ol), ethyllinalool, benzyl salicylate, 2-methyl-3-(4-tert-butylphenyl) propanal (Lysmeral), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super), hexyl salicylate, 4-tert-butylcyclohexyl acetate (Oryclone), 2-tert-butylcyclohexyl acetate (Agrumex HC), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral), alpha-amylcinnamaldehyde, ethylene brassylate, (E)- and/or (Z)-3-methylcyclopentadec-5-enone (Muscenon), 15-pentadec-11-enolide and/or 15-pentadec-12-enolide (Globalide), 15-cyclopentadecanolide (Macrolide), 1-(5,6,7,8-tetrahydro-3,5,5,6,8,8-hexamethyl-2-naphthalenyl) ethanone (Tonalid), 2-isobutyl-4-methyltetrahydro-2H-pyran-4-ol (Florol), 2-ethyl-4-(2,2,3-trimethyl-3-cyclopenten-1-yl)-2-buten-1-ol (Sandolen), cis-3-hexenyl acetate, trans-3-hexenyl acetate, trans-2/cis-6-nonadienol, 2,4-dimethyl-3-cyclohexenecarboxaldehyde (Vertocitral), 2,4,4,7-tetramethyloct-6-en-3-one (Claritone), 2,6-dimethyl-5-hepten-1-al (Melonal), borneol, 3-(3-isopropylphenyl) butanal (Florhydral), 2-methyl-3-(3,4-methylenedioxyphenyl) propanal (Helional), 3-(4-ethylphenyl)-2,2-dimethylpropanal (Florazon), 7-methyl-2H-1,5-benzodioxepin-3 (4H)-one (Calone), 3,3,5-trimethylcyclohexyl acetate (preferably with a content of cis isomers of 70% by weight) or more and 2,5,5-trimethyl-1,2,3,4,4a,5,6,7-octahydro-naphthalen-2-ol (Ambrinol S), 3-(4-tert-butylphenyl)-propanal (Bourgeonal), ethyl 2-methylpentanoate (Manzanate), ethoxymethoxycyclododecane (Amberwood), 2,4-dimethyl-4,4a,5,9b-tetrahydroindeno[1,2-d][1,3]dioxine (Magnolan), (2-tert-butylcyclohexyl) acetate (Verdox), 3-[5,5,6-trimethylbicyclo[2.2.1]hept-2-yl]cyclohexan-1-ol (Sandela), methyl benzoate, benzyl acetate, linalool, ethylvanillin, 2,5-dimethyl-4-hydroxy-2H-furan-3-one (furaneol), 3-hydroxy-2-methyl-4H-pyran-4-one (maltol), essential oils, concretes, absolutes, resins, resinoids, balsams, tinctures selected from the group consisting of ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; hyssop oil; civet absolute; cinnamon leaf oil; cinnamon bark oil, fractions of the aforementioned oils, concretes, absolutes, resins, resinoids, balsams or tinctures, or ingredients isolated from the aforementioned oils, concretes, absolutes, resins, resinoids, balsams, or tinctures, individual fragrances from the group of hydrocarbons selected from the group consisting of 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; and diphenylmethane, aliphatic alcohols selected from the group consisting of hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; and 4-methyl-3-decen-5-ol; aliphatic aldehydes and acetals thereof selected from the group consisting of hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronelly-loxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; and 6-methyl-5-hepten-2-one;

aliphatic sulfur-containing compounds selected from the group consisting of 3-methylthiohexanol; 3-methylthiohexyl acetate; 3-mercaptohexanol; 3-mercaptohexyl acetate; 3-mercaptohexyl butyrate; 3-acetylthiohexyl acetate; and 1-menthene-8-thiol; aliphatic nitriles selected from the group consisting of 2-nonenenitrile; 2-undecenenitrile; 2-tridecenenitrile; 3,12-tridecadienenitrile; 3,7-dimethyl-2,6-octadienenitrile; and 3,7-dimethyl-6-octenenitrile esters of aliphatic carboxylic acids selected from the group consisting of (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; and 4-methyl-2-pentyl crotonate;

acyclic terpene alcohols selected from the group consisting of geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; and 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates of the aforementioned alcohols;

acyclic terpene aldehydes and ketones selected from geranial; neral; citronellal; 7 hydroxy-3,7-dimethyloctanal; 7 methoxy-3,7-dimethyloctanal; 2,6,10-trimethyl-9 undecenal; geranyl acetone; as well as the dimethyl and diethylacetals of geranial, neral, 7-hydroxy-3,7-dimethyloctanal;

cyclic terpene alcohols selected from menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

cyclic terpene aldehydes and ketones selected from the group consisting of menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8 (5H)-one; 2-methyl-4-(2,6,6-trimethyl-1-cyclohexen-1-yl)-2-butenal; nootkatone;

dihydronootkatone; 4,6,8-megastigmatrien-3-one; alpha-sinensal; beta-sinensal; and acetylated cedar wood oil (methyl cedryl ketone);

cyclic alcohols selected from the group consisting of 4-tert-butylcyclohexanol; 3,3,5-trimethylcyclohexanol; 3-isocamphylcyclohexanol; 2,6,9-trimethyl-Z2,Z5,E9-cyclododecatrien-1-ol; and 2-isobutyl-4-methyltetrahydro-2H-pyran-4-ol;

cycloaliphatic alcohols selected from the group consisting of alpha-3,3-trimethylcyclohexylmethanol; 1-(4-isopropylcyclohexyl) ethanol; 2-methyl-4-(2,2,3-trimethyl-3-cyclopent-1-yl) butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl) pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl) pentan-3-ol; and 1-(2,2,6-trimethylcyclohexyl) hexan-3-ol;

cyclic and cycloaliphatic ethers selected from the group consisting of cineol; cedryl methyl ether; cyclododecyl methyl ether; 1,1-dimethoxycyclododecane; (ethoxymethoxy) cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b] furan; 1,5,9-trimethyl-13-oxabicyclo-[10.1.0]trideca-4,8-diene; rose oxide; and 2-(2,4-dimethyl-3-cyclohexen-1-yl)-5-methyl-5-(1-methylpropyl)-1,3-dioxane;

cyclic and macrocyclic ketones selected from the group consisting of 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4 (5H)-indanone; 8-cyclo-hexadecen-1-one; 7-cyclohexadecen-1-one; (7/8)-cyclohexadecen-1-one; 9-cyclo-heptadecen-1-one; cyclopentadecanone; and cyclohexadecanone;

cycloaliphatic aldehydes selected from the group consisting of 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; and 4-(4-methyl-3-penten-1-yl)-3-cyclohexenecarbaldehyde;

cycloaliphatic ketones selected from the group consisting of 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; and tert-butyl (2,4-dimethyl-3-cyclohexen-1-yl) ketone;

esters of cyclic alcohols selected from the group consisting of 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate;

decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; and 4,7-methanooctahydro-5 or 6-indenyl acetate;

esters of cycloaliphatic alcohols selected from 1-cyclohexylethyl crotonate;

esters of cycloaliphatic carboxylic acids selected from the group consisting of allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; and ethyl 2-methyl-1,3-dioxolane-2-acetate;

araliphatic alcohols selected from the group consisting of benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl) propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; and 1-(4-isopropylphenyl) ethanol;

esters of araliphatic alcohols and aliphatic carboxylic acids selected from the group consisting of benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; and 4-methoxybenzyl acetate;

araliphatic ethers selected from the group consisting of 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; and 4,4,5,9b-tetrahydro-2,4-dimethylindeno[1,2-d]-m-dioxine;

aromatic and araliphatic aldehydes selected from the group consisting of benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl) propanal; 2-methyl-3-(4-tert-butylphenyl) propanal; 2-methyl-3-(4-isobutylphenyl) propanal; 3-(4-tert-butylphenyl) propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxy-benzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl) propanal; and 2-methyl-3-(4-methylenedioxyphenyl) propanal;

aromatic and araliphatic ketones selected from the group consisting of acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl) ethanone; 2-benzofuranylethanone; (3-methyl-2-benzofuranyl) ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; and 5',6',7',8'-tetrahydro-3',5',5',6',8',8'-hexamethyl-2-acetonaphthone;

aromatic and araliphatic carboxylic acids and esters thereof selected from the group consisting of benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; and ethyl 3-methyl-3-phenylglycidate; nitrogen-containing aromatic compounds selected from the group consisting of 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl) propanal or 2,4-dimethyl-3-cyclohexenecarbaldehyde; 6-isopropylquinoline; 6-isobutylquinoline; 6-sec-butylquinoline; 2-(3-phenylpropyl) pyridine; indole; skatole; 2-methoxy-3-isopropylpyrazine; and 2-isobutyl-3-methoxypyrazine; phenols, phenyl ethers and phenyl esters selected from the group consisting of estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl) phenol; and p-cresyl phenylacetate; heterocyclic compounds selected from the group consisting of 2,5-dimethyl-4-hydroxy-2H-furan-3-one; 2-ethyl-4-hydroxy-5-methyl-2H-furan-3-one; 3-hydroxy-2-methyl-4H-pyran-4-one; and 2-ethyl-3-hydroxy-4H-pyran-4-one;

lactones selected from the group consisting of 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; and octahydrocoumarin;

and mixture of two or more of these aroma chemicals.

13. The composition according to claim 12, wherein the at least one aroma chemical (i) which is different from (3-hydroxy-2,2-dimethyl-propyl) acetate and (3-acetoxy-2,2-dimethyl-propyl) acetate is selected from the group consisting of:

geranyl acetate (3,7-Dimethyl-2,6 octadien-1yl acetate), alpha-hexylcinnamaldehyde, 2-phenoxyethyl isobutyrate (Phenirat), dihydromyrcenol (2,6-dimethyl-7-octen-2-ol), methyl dihydrojasmonate (Hedione, Hedione HC), 4,6,6,7,8,8-hexamethyl-1,3,4,6,7,8-hexahydro-cyclopenta[g]benzopyran (Galaxolid), tetrahydrolinalool (3,7-dimethyloctan-3-ol), ethyllinalool, citronellol, citronellyl acetate, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethyl-naphthalene (Iso E Super), hexyl salicylate, 4-tert-butylcyclohexyl acetate (Oryclone), coumarin, 2-phenylethyl alcohol, ethylene brassylate, (E)- and/or (Z)-3-methylcyclopentadec-5-enone (Muscenon), 15-cyclo-pentadecanolide (Macrolide), 1-(5,6,7,8-tetrahydro-3,5,5,6,8,8-hexamethyl-2-naphthalenyl) ethanone (Tonalid), 2-isobutyl-4-methyltetrahydro-2H-pyran-4-ol (Florol), 2-ethyl-4-(2,2,3-trimethyl-3- cyclopenten-1-yl)-2-buten-1-ol (Sandolen), cis-3-hexenyl acetate, trans-3-hexenyl acetate, trans-2/cis-6-nonadienol, 2,4-dimethyl-3-cyclohexenecarboxaldehyde (Vertocitral), 3-(4-ethylphenyl)-2,2-dimethylpropanal (Florazon), 7-methyl-2H-1,5-benzodioxepin-3 (4H)-one (Calone), ethyl 2-methylpentanoate (Manzanate), (2-tert-butyl-cyclohexyl) acetate (Verdox), benzyl acetate, linalool, ethylvanillin, bergamot oil; cedar wood oil; lemon oil; davana oil; *galbanum* oil; galbanum resin; grapefruit oil; ginger oil; lavandin absolute; lavandin oil; mandarin oil; clary sage oil; orange blossom absolute; orange oil; patchouli oil; pepper oil; vetiver oil; limonene; (E)-2-hexenol; (E)- and (Z)-3-hexenol; 4-methyl-3-decen-5-ol; hexanal; octanal; nonanal; decanal; 1,1-dimethoxy-2,2,5-trimethyl-4-hexene; 5-methyl-3-heptanone oxime; ethyl acetoacetate; isoamyl acetate; hexyl acetate; 3-methyl-2-butenyl acetate; (E)- and (Z)-3-hexenyl acetate; ethyl butyrate; ethyl hexanoate; allyl hexanoate; ethyl heptanoate; allyl heptanoate; geraniol; nerol; linalool; geranial; neral; alpha-terpineol; isobornyl acetate; beta-ionone; alpha-damascone; beta-damascone; beta-damascenone; delta-damascone; nootkatone; cedar wood oil (methyl cedryl ketone); 3-methyl-5-(2,2,3-trimethyl-3-cyclopenten-1-yl) pentan-2-ol; cedryl methyl ether; 3a,6,6,9a-tetramethyldodecahydronaphtho[2,1-b]furan; rose oxide; 6,7-dihydro-1,1,2,3,3-pentamethyl-4 (5H)-indanone; 1-(5,5-dimethyl-1-cyclohexen-1-yl)-4-penten-1-one; 4,7-methano-3a,4,5,6,7,7a-hexahydro-5 or 6-indenyl propionate; 4,7-methanooctahydro-5 or 6-indenyl acetate; allyl 3-cyclohexylpropionate; ethyl 2-methyl-1,3-dioxolane-2-acetate; 1-phenylethyl alcohol, 2-phenylethyl alcohol, benzyl acetate; 2-phenylethyl isobutyrate; 1-phenylethyl acetate; alpha,alpha-dimethylphenylethyl acetate; alpha,alpha-dimethylphenylethyl butyrate; 2-phenoxyethyl isobutyrate; 2,4,6-trimethyl-4-phenyl-1,3-dioxane; 3-(4-ethylphenyl)-2,2-dimethylpropanal; 2-methyl-3-(4-isobutylphenyl) propanal; cinnamaldehyde; alpha-hexylcinnamaldehyde; 4-methoxybenzaldehyde; 4-(4-hydroxyphenyl)-2-butanone; methyl benzoate; phenylethyl phenylacetate; phenylethyl cinnamate; hexyl salicylate; methyl 2,4-dihydroxy-3,6-dimethylbenzoate; ethyl 3-phenylglycidate; ethyl 3-methyl-3-phenylglycidate; eugenol; 2-ethyl-3-hydroxy-4H-pyran-4-one; 1,4-decanolide; 1,4-undecanolide; 1,15-pentadecanolide; cis- and trans-11-pentadecen-1,15-olide; cis- and trans-12-pentadecen-1,15-olide; coumarin;

and mixtures of two or more of these aroma chemicals.

14. The composition according claim 12, wherein the composition is selected from the group consisting of perfume compositions, body care compositions, hygiene articles, cleaning compositions, textile detergent compositions, compositions for scent dispensers, foods, food supplements, pharmaceutical compositions and crop protection compositions.

15. The composition according claim 12, wherein (3-hydroxy-2,2-dimethyl-propyl) acetate is used in an amount of 0.01 wt. % to 15 wt. % of (3-hydroxy-2,2-dimethyl-propyl) acetate based on the total weight of (3-hydroxy-2,2-dimethyl-propyl) acetate and (3-acetoxy-2,2-dimethyl-propyl) acetate.

* * * * *